US00PP18061P3

(12) United States Plant Patent
Mortko

(10) Patent No.: US PP18,061 P3
(45) Date of Patent: Sep. 18, 2007

(54) ***HOSTA* PLANT NAMED 'STITCH IN TIME'**

(50) Latin Name: *Hosta*
Varietal Denomination: Stitch in Time

(76) Inventor: Robert A. Mortko, 16370 W. 138th Terr, Olathe, KS (US) 66062

( * ) Notice: Subject to any disclaimer, the term of this patent is extended or adjusted under 35 U.S.C. 154(b) by 0 days.

(21) Appl. No.: 11/331,876

(22) Filed: Jan. 17, 2006

(65) Prior Publication Data

US 2007/0169242 P1 Jul. 19, 2007

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent Bell
*Assistant Examiner*—Annette H Para

(57) ABSTRACT

A new and distinct cultivar of *Hosta* named 'Stitch in Time', characterized by its wide yellow colored leaf margins and its unique gathering and stitching where the yellow leaf margin tissue meets the dark green center tissue.

1 Drawing Sheet

DESCRIPTION

BACKGROUND OF THE INVENTION

The present invention relates to a new and distinct cultivar of *Hosta* plant, botanically known as *Hosta,* hereinafter referred to by the cultivar name 'Stitch in Time'.

The new plant was discovered by the Inventor during the summer of 2003 as a non-induced, naturally occurring whole plant mutation of *Hosta* 'Summer Breeze' (not patented) at his nursery in Olathe, Kans., USA. Asexual propagation of the new cultivar by division in 2004 in Olathe, Kans. and by tissue culture in 2005 in Waseca, Minn., has shown the unique and distinct characteristics of this new plant are stable and reproduce true to type in successive generations.

SUMMARY OF THE INVENTION

The following traits have been repeatedly observed and are determined to be the unique characteristics of 'Stitch in Time'. These characteristics in combination distinguish the new *Hosta* as a new and unique cultivar:

1. Medium sized clump;
2. Dark green narrow-centered leaves with a very wide yellow margin which comprises approximately 80% of the leaf area;
3. A unique gathering or stitching effect where the green and yellow leaf tissues meet; and
4. Pale lavender flowers.

The new *Hosta* can be compared to its parent cultivar, 'Summer Breeze'. In the new *Hosta,* the margin width is substantially wider than in the *Hosta* 'Summer Breeze'. The green center of the new *Hosta* is reduced proportionately to the increased margin. In addition the parent plant does not show the unique gathering or stitching effect where the green and yellow leaf tissue meets.

The new *Hosta* cultivar has not been observed under all possible environmental conditions. The phenotype may vary to some extent with variations in environmental conditions such as temperature, fertility and light intensity, but without any variance in the genotype.

BRIEF DESCRIPTION OF THE PHOTOGRAPHS

The accompanying color photographs illustrate the overall appearance of the new cultivar including its unique traits as a three year old plant growing in a one gallon container. The colors are as true as is reasonably possible with conventional photography.

Figure 1:
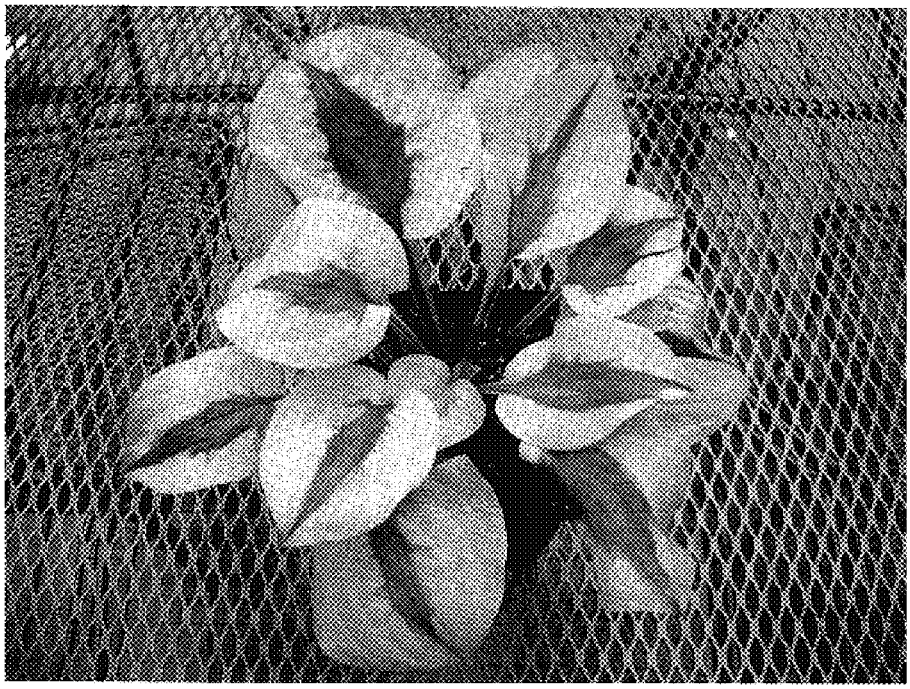

FIG. 1 was taken in July and comprises a top perspective of a typical plant of the new *Hosta.*

Figures 2, 3:
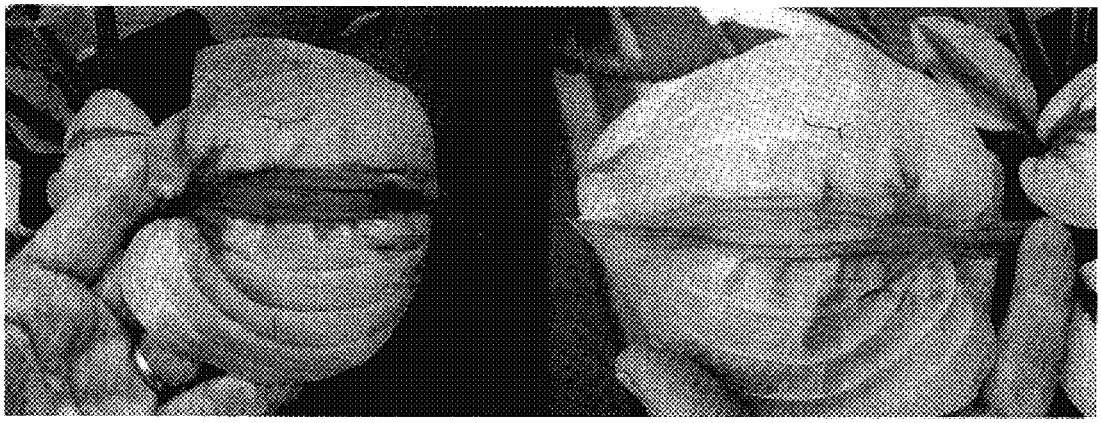

FIG. 2 was taken in October and shows the front side of an individual leaf with the unique stitching effect between the center and margin tissue.

FIG. 3 was taken in October and shows the back side of an individual leaf.

DETAILED DESCRIPTION OF THE INVENTION

In the following description, color references are made to The Royal Horticultural Society's Colour Chart (1995 edition) except where general terms of ordinary dictionary significance are used. The following observations and measurements describe a three-year old plant growing in a one gallon container, as depicted in the accompanying photographs, which was grown outdoors in Olathe, Kans., USA.

Botanical classification: *Hosta* 'Stitch in Time'.
Parentage: Naturally occurring whole plant mutation of *Hosta* 'Summer Breeze' (non patented.
Propagation:
*Method.*—By division and tissue culture.
Plant description:
*Plant habit.*—Compact, mounding, symmetrical.
*Culture.*—Light to medium shade in moist soil.
*Plant type.*—Herbaceous rhizomatous perennial.
*Plant height.*—20 cm (up to about 46 cm at maturity).
*Plant width.*—38 cm (up to about 107 cm at maturity).
*Vigor and growth rate.*—Moderate.
*Root system.*—Normal, fleshy, branching.
*Disease resistance.*—No known resistance or susceptibility to disease known to *Hosta* has been observed.

Foliage description:

*Leaf shape.*—Broadly ovate with a cordate base.

*Leaf margin.*—Entire.

*Leaf surface.*—Slightly dull on top and slightly shiny on bottom.

*Leaf texture.*—Glabrous, moderate to heavy substance, slightly wavy leaf margins.

*Leaf size.*—10 cm in width, 11 cm in length (increasing to about 18 cm in width and 22 cm in length at maturity).

*Venation pattern.*—Campylodrome with 6 to 8 pairs of veins (increasing to 10–12 vein pairs at maturity). Venation pattern becomes very irregular and contorted in the green centered tissue area.

*Leaf color.*—Dark green center (about RHS 138B) with a very wide golden yellow margin (about RHS 3C). The leaf margin comprises about 80% of the leaf surface and changes to a greenish yellow (about RHS 151D) late in the season.

Petiole description: Plant petioles may have a length of approximately 15 cm with a width of about 13 to 19 mm. The petiole has a central region with a dark green color (about RHS 138B) with a margin having a golden yellow color (about RHS 3C).

Flower scape description:

*Scape shape.*—Round, solid.

*Scape number.*—Each mature eye comprising the clump may produce a single flower scape under normal growing conditions.

*Scape posture.*—Straight, held upright at about 10 to 30 degrees from vertical.

*Scape size.*—About 46 to 76 cm in length, about 5 mm in diameter.

*Scape color.*—Dark green (about RHS 138B).

*Scape surface.*—Glabrous.

*Leaf bracts.*—None observed.

Flower description:

*Inflorescence type.*—Terminal racemes of single funnel-shaped flowers on elongated scapes.

*Lastingness of inflorescence.*—About 4 weeks in midsummer from first opening bloom to fading of last opening bloom, individual blooms last about one day.

*Flower shape.*—Funnel-shaped.

*Flower number.*—The number of flowers per raceme varies from about 15 to 30.

*Flower internode length.*—About 2 cm.

*Flower fragrance.*—None detected.

*Flower bud shape.*—Spathulate.

*Flower bud size.*—About 3 cm in length and 1.3 cm in diameter.

*Flower bud color.*—Pale lavender (about RHS 85D).

*Flower size.*—About 5.5 cm in length and 3 cm in diameter.

*Flower color.*—Pale lavender (about RHS 85D).

*Pedicels.*—About 5 mm in length, 2 mm in diameter, RHS 138B in color, glabrous surface.

*Perianth features.*—Comprised of 6 tepals, 3 internal and 3 external, overlapping in expanded region and fused in tube region.

*Tepal shape.*—Oblanceolate with acute apex.

*Tepal size.*—About 5 cm in length and 1 cm in width.

*Tepal color.*—Pale lavender (about RHS 85D).

*Tepal texture.*—Glabrous.

*Floral bracts.*—1 per flower, ovate in shape, glabrous surface, RHS 138B in color, about 3.5 cm in length and 1 cm in width.

Reproductive organ description:

*Gynoecium.*—1 pistil; style is about 5.5 cm in length, 1 mm in diameter, white in color; stigma is 3-lobed and white in color; ovary is superior, compound, composed of 3 locules, RHS 146D in color.

*Androecium.*—6 stamens; filament is about 5 cm in length, 1 mm in diameter, white in color; anthers are about 3 mm in length, 1 mm in width, RHS 202A in color; pollen is abundant and RHS 15B in color.

*Fruit.*—Not observed under growing conditions tested.

*Seeds.*—Not observed under growing conditions tested.

Root development: From transfer to rooting media in tissue culture, rooting takes approximately 4 weeks at about 20 degrees Celsius. After transfer from stage III in tissue culture to planting into soil in a greenhouse, a well rooted plant is produced in approximately 8 weeks with a daytime temperature of about 20 degrees Celsius and a soil temperature of about 26 degrees Celsius.

I claim:

1. A new and distinct cultivar of *Hosta* plant named 'Stitch in Time' as illustrated and described herein.

* * * * *

Hosta 'Stitch in Time' (summer color, July 17th)

Front and back of leaf (fall color, Oct 23rd)